United States Patent [19]
Kambara et al.

[11] Patent Number: 5,534,655
[45] Date of Patent: Jul. 9, 1996

[54] PROCESS FOR PREPARING ACRYLAMIDE

[75] Inventors: Yoshihiko Kambara; Yoshikazu Uehara; Takeya Abe; Koichi Asao, all of Osaka, Japan

[73] Assignee: Mitsui Toatsu Chemicals, Inc., Tokyo, Japan

[21] Appl. No.: 392,508

[22] Filed: Feb. 23, 1995

[30]     Foreign Application Priority Data

Feb. 3, 1994  [JP]  Japan .................................. 6-032094

[51] Int. Cl.$^6$ ................................................. C07C 231/06
[52] U.S. Cl. ......................... 564/127; 564/126; 564/128
[58] Field of Search .................................... 564/127, 128, 564/126

[56]             References Cited

U.S. PATENT DOCUMENTS

| 3,943,171 | 3/1976 | Hoffmann et al. | 564/128 |
| 3,962,333 | 6/1976 | Yoshimura et al. | 564/128 |
| 4,820,872 | 4/1989 | Farrar et al. | 564/128 |

FOREIGN PATENT DOCUMENTS

| 515123 | 5/1992 | European Pat. Off. . |
| 50-12409 | 5/1975 | Japan . |
| 54-73727 | 6/1979 | Japan . |
| 61-21220 | 5/1986 | Japan . |
| 63-203654 | 8/1988 | Japan . |
| 4-57663 | 9/1992 | Japan . |
| 2061977 | 6/1980 | United Kingdom . |

OTHER PUBLICATIONS

Chemical Abstracts, vol. 83, No. 16, Abstract No. 132340j, H. Oogiri et al, "Polyacrylamides", p. 30, column 2, 1979–JP–A–7567190 Abstract.
Chemical Abstracts, vol. 91, No. 16, Abstract No. 124204t, Y. Kageyama et al, "Acrylamide", p. 16, column 1, 1979–JP–A–7973727 Abstract.
Chemical Abstracts, vol. 91, No. 16, Abstract No. 124198u, Y. Kageyama et al, "Acrylamide", p. 15, column 2, 1979–JP–A–7966618 Abstract.

*Primary Examiner*—Shailendra Kumar
*Attorney, Agent, or Firm*—Burns, Doane, Swecker & Mathis

[57]                ABSTRACT

A process for preparing acrylamide is disclosed herein which comprises subjecting acrylonitrile to a hydration reaction in the presence of a copper-based catalyst, said process comprising the step of allowing a compound having an active methylene group and an acidic group in one molecule or a salt of the compound, for example, malonic acid, cyanoacetic acid or its salt to be present in a reaction system. According to the hydration reaction, it is possible to inhibit the secondary formation of impurities which cannot be heretofore removed, without any deterioration of a catalyst activity, and acrylamide can be obtained which is useful as a material for the manufacture of a high-molecular weight flocculant having a sufficiently large molecular weight and a good water solubility.

13 Claims, No Drawings

PROCESS FOR PREPARING ACRYLAMIDE

BACKGROUND OF THE INVENTION

1. Field of the Invention

The present invention relates to a process for preparing acrylamide by bringing acrylonitrile into contact with water in the presence of a copper-based catalyst to hydrate acrylonitrile. More specifically, it relates to a process for preparing high-quality acrylamide which permits the manufacture of a polymer having a sufficiently high molecular weight and good water solubility.

2. Description of the Related Art

Acrylamide has been heretofore used in the form of an acrylamide polymer in papermaking chemicals, flocculants, oil recovery agents and the like, and in addition, it has many uses as a comonomer for various kinds of polymers. In the old days, acrylamide for these uses was manufactured by the so-called sulfuric acid method, but in recent years, a contact hydration method which comprises carrying out a reaction in the presence of a copper-based catalyst has been developed. Nowadays, this catalytic hydration method has been industrially practiced instead of the sulfuric acid method.

Among the above-mentioned uses of acrylamide, particularly the flocculants here also recently applied to the treatment of waste water, and in consequence, substantial efforts have been made to improve the quality and performance of acrylamide. Above all, with regard to the acrylamide polymer which can be used as the flocculants, there is a remarkable tendency that its molecular weight which is considered to have a direct influence on the performance is increased, and in recent years, an acrylamide polymer having a high molecular weight of about 10,000,000 or more, particularly about 15,000,000 is required. This molecular weight is much higher as compared with a molecular weight of usually 1,000,000 or less which is required for the acrylamide polymer for other uses or another polymer. In addition, since the obtained acrylamide polymer is usually dissolved in water when used as the flocculants, it is necessary that the acrylamide polymer is promptly dissolved without leaving insolubles. Furthermore, in view of an acrylamide monomer being poisonous, it is required that the unreacted monomer in the polymer be minute, for example, 0.2% by weight or less.

These requirements are incompatible with the increase of the molecular weight, and in order to meet both of them, substantial efforts have now been made. Although this high-molecular acrylamide polymer is only one use of acrylamide, if such acrylamide is not suitable for this use, it is not apppplicable for general use. The present invention is concerned with a process for preparing acrylamide which is applicable to many uses inclusive of this use.

The molecular weight referred to in the present invention is a value measured by a test procedure shown in Example 1 which will be hereinafter described. In the case that the polymer obtained in an aqueous medium is dried to form a dry powder having a water content of 20% by weight or less, particularly 10% by weight or less and this dry powder is then used, much attention is paid to water solubility, and the water solubility referred to in the present invention is also mainly employed in this meaning.

The preparation of the acrylamide polymer having the high molecular weight and the sufficient water solubility depends largely upon not only the preparation process of the polymer, but also the quality of the acrylamide. Therefore, in preparing acrylamide from acrylonitrile by the catalytic hydration method, for the purpose of inhibiting the formation of by-products, various methods regarding the improvement of synthetic reaction systems have been reported. In the preparation of acrylamide, it is necessary to sufficiently purify acrylamide, and usually the purification of acrylamide is carried out through an ion exchange resin. However, some kinds of impurities cannot be removed by conventional ion exchange resin purification, and for the sake of the preparation of higher-quality acrylamide, some methods have been suggested.

For example, Japanese Patent Publication No. 12409/1975 (corresponding to U.S. Pat. Nos. 3,911,009 and 3,962,333) have suggested a method in which a copper salt such as copper nitrate or copper acetate is added to a synthetic reaction system to remarkably improve the activity of a copper catalyst, and instead of adding the copper salt, a part of the copper catalyst may be converted into a copper salt, and for this conversion, an inorganic acid or an organic acid is added. In this case, metallic copper is required to be partially oxidized prior to use or simultaneously. Moreover, on pages 23 to 24 of Khim. Technol., 1983 (3), it is described that sulfuric acid or acrylic acid is added to a system using a reduced copper catalyst, thereby improving the reaction rate and selectivity, and this is due to a salt formed by a reaction of the acid with oxides of copper.

Furthermore, according to Japanese Patent Laid-Open No. 57663/1992 corresponding to U.S. Pat. No. 4,820,872 (PCT WO 86/00614), there has been suggested a method in which an oxidizing agent and an oxidized catalyst are dissolved and removed or reducing agent is added, in the presence of a catalyst such as Raney copper; and concretely, a combination of copper nitrate and an organic acid such as acetic acid is described. In consequence, the formation of by-products can be inhibited.

Japanese Patent Laid-open No. 203654/1988 has described that nitric acid or a nitrate and (meth)acrylic acid and/or its salt are added to a synthetic reaction system to prevent the activity of a catalyst and the quality of a monomer from deteriorating. In addition, in preparing acrylamide, a stable operation is possible for a long period of time.

Japanese Patent Publication No. 21220/1986 has described that at least one material selected from the group consisting of ammonia, ureas, aromatic amines, primary and secondary lower alkylamines, and primary and secondary lower alkanolamines is added to a synthetic reaction system to particularly inhibit the secondary formation of impurities which cannot be removed by a conventional ion exchange resin treatment, and an acrylamide polymer which can be prepared from acrylamide obtained under such conditions has a high molecular weight and a sufficient water solubility. Moreover, a strongly acidic cation exchange resin is used in the purification step of acrylamide, whereby these additives can be easily removed.

According to Japanese Patent Laid-open No. 73727/1979, a phenol substituted at its meta-position is added to a synthetic reaction system, whereby the secondary formation of impurities which cannot be removed by a conventional ion exchange resin treatment can be inhibited. Furthermore, a strongly basic anion exchange resin is used in the purification step of acrylamide to easily remove the above-mentioned additive, and an acrylamide polymer which can be prepared from acrylamide obtained under such conditions has a high molecular weight and a sufficient water solubility.

However, Japanese Patent Publication No. 12409/1975 has described a method for preparing acrylamide which comprises bringing acrylonitrile into contact with water in the presence of a copper-based catalyst to hydrate acrylonitrile, and in this case, nitric acid or a nitrate is added. This method is excellent as a means for maintaining and improving a catalyst activity. However, probably due to the accumulation of copper oxidized in a reactor with the elapse of time, it has been admitted that the secondary formation of impurities such as ethylene cyanohydrin increases and the activity of the catalyst deteriorates. The quality of acrylamide can be evaluated on the basis of the water solubility and the molecular weight of the prepared acrylamide polymer, but the quality of acrylamide obtained by this method deteriorates with time.

A method for dissolving copper oxides accumulated in the reactor with an acid or the like disclosed in the above-mentioned Japanese Patent Publication No. 12409/1975, pages 23 to 24 of Khim. Tekhnol., 1983 (3), and Japanese Patent Publication No. 57663/1992 (PCT WO 86/00614) is effective to decrease ethylene cyanohydrin and the like which are impurities caused by the presence of copper oxides. However, the catalyst activity cannot be recovered only by dissolving the copper oxides of the catalyst with acid whose activity has once deteriorated due to the formation of the copper oxides, and in a certain case, the activity further deteriorates. The quality of acrylamide obtained by these methods, i.e., the water solubility and the molecular weight of a polymer obtained by its polymerization are not improved, and when a certain kind of acid is used, it has been admitted that the quality conversely deteriorates.

In the method disclosed in the above-mentioned Japanese Patent Publication No. 21220/1986, at least one material selected from the group consisting of ammonia, ureas, aromatic amines, primary and secondary lower alkylamines, and primary and secondary lower alkanolamines is added to a synthetic reaction system, the catalyst activity noticeably deteriorates and the quality of acrylamide is hardy improved, the reason is probably that the added compound has been absorbed by the catalyst.

In the method of Japanese Patent Application Laid-open No. 73727/1979, a phenol substituted at its meta-position is added to a synthetic reaction system, the deterioration of the catalyst activity does not take place, and when acrylamide prepared by this method is treated with a strongly basic anion exchange resin, the phenol substituted at the meta-position can be removed. The quality of the thus obtained acrylamide is admitted to be higher than that of acrylamide obtained by the method described in Japanese Patent Publication No. 21220/1986 which comprises adding an amine to a synthetic reaction system, but the quality is still insufficient. In addition, the phenol substituted at the meta-position can be removed with a strongly basic anion exchange resin only, and in a removal step, acrylamide itself hydrolyzes to form acrylic acid, so that the exchange capacity of the resin noticeably deteriorates. Moreover, the regeneration of the resin is difficult, and acrylamide is liable to polymerize in the resin layer during the feed of an aqueous acrylamide solution. In consequence, acrylamide obtained by this method is not practical.

SUMMARY OF THE INVENTION

The present inventors have intensively investigated an additive to be added to a synthetic reaction system in preparing acrylamide by bringing acrylonitrile into contact with water in the presence of a copper-based catalyst to hydrate acrylonitrile for the purpose of obtaining a sufficient water solubility and molecular weight characteristics of an acrylamide polymer which can be formed by polymerizing acrylamide. As a result, it has been found that the secondary formation of impurities which cannot be removed by a conventional ion exchange resin treatment can be inhibited by adding a compound having an active methylene group and an acidic group in one molecule or a salt of the compound to the reaction system; the added additive can be easily removed by the use of a weakly basic or a medially basic anion exchange resin; and an acrylamide polymer prepared from the thus obtained acrylamide has a high molecular weight and a sufficient water solubility. In consequence, the present invention has now been completed.

That is to say, the present invention is directed to a process for preparing acrylamide by subjecting acrylonitrile to a hydration reaction in the presence of a copper-based catalyst, said process comprising the step of allowing a compound having an active methylene group and an acidic group in one molecule or a salt of the compound to be present in a reaction system.

When the compound having the active methylene group and the acidic group or a salt of the compound is added in accordance with the above-mentioned process of the present invention, it is possible to inhibit the secondary formation of impurities which cannot be heretofore removed, without any deterioration of the catalyst activity, and high-quality acrylamide can be obtained which permits the formation of an excellent flocculant having a sufficiently large molecular weight and a good water solubility.

DETAILED DESCRIPTION OF THE INVENTION

Next, reference will be made to the gist of a process for preparing acrylamide of the present invention.

Examples of a copper-based catalyst for use in the present invention include (A) a combination of copper in the form of copper wire or copper powder with copper ions;

(B) a copper-base of catalyst (reduced copper) by reducing a copper compound with a reducing agent;

(C) a copper-based catalyst (copper as a decomposed copper) obtained by decomposing a copper compound with heat or the like, and (D) a copper-based catalyst (Raney copper) obtained by dissolving the aluminum out of a Raney alloy with an alkali or the like. It can be presumed that the main component of any one of these catalysts is an elemental copper.

The copper-based catalyst may be supported on a conventional carrier, and it may contain a metal other than copper, for example, chromium or molybdenum.

It is desirable to avoid the contact of the catalyst with oxygen or an gas containing oxygen before and after the use of the catalyst, because if the catalyst comes in contact with oxygen at a time of the use or reuse, the activity of the catalyst is lost and the formation of a by-product such as ethylene cyanohydrin is increased.

The hydration reaction of acrylonitrile in the present invention is carried out in the presence of the above-mentioned copper-based catalyst as follows. The reaction is carried out continuously or batchwise in a liquid phase while using the catalyst in the form of a suspended bed or fixed bed. The weight ratio of acrylonitrile to water, both to be used during hydration, can be determined practically as desired. The preferred weight ratio may be in a range of from 60:40 to 5:95, more preferably 50:50 to 10:90. The conversion of acrylonitrile is preferably in a range of from 10 to 98%, more preferably from 30 to 95%. The reaction temperature in the hydration reaction of acrylonitrile with water is preferably in a range of from 50° to 200° C., more preferably from 70° to 150° C.

In a reactor, there is maintained a pressure based on a vapor pressure due to the above-mentioned temperature and composition or based on this vapor pressure and the addition of an inert gas such as nitrogen. Thus, the pressure in the reactor is usually in the range of from atmospheric pressure to 10 atm.

Dissolved oxygen, contained in materials such as the catalyst, acrylonitrile and water which are fed to the reactor impairs the activity of the catalyst and increases the occurrence of by-product such as ethylene cyanohydrin, and therefore it is also desired to maintain the interior of the reactor under an oxygen-free atmosphere. After the hydration reaction, a liquid reaction mixture is taken out of the reactor, and this solution mainly contains unreacted acrylonitrile, unreacted water, acrylamide, a by-product such as ethylene cyanohydrin and copper.

The reaction solution obtained by the above-mentioned reaction, if necessary, is subjected to a usual vaporization or distillation operation to obtain a concentrated aqueous acrylamide solution, and unreacted acrylonitrile and water as distillates. These recovered material can be used again as fresh reaction materials.

Here, the reaction solution which has not undergone the concentration and the aqueous acrylamide solution which has undergone the concentration will be called the solution containing acrylamide.

The aqueous acrylamide solution obtained by concentrating the reaction solution (hereinafter referred to simply as "aqueous acrylamide solution") is then subjected to a suitable purification step such as a cation exchange treatment, a chelate resin treatment, an anion exchange treatment, an air or oxygen gas treatment or an active carbon treatment. In addition, there can also be employed the so-called synthetic adsorption resin (e.g., trade name Adsorbent Resin, made by Hokuetsu Carbon Industry Co., Ltd.) which can be used in about the same manner as in the case of the active carbon or the ion exchange resin. In the middle of this purification step or after this step, the aqueous acrylamide solution may be subjected to the above-mentioned concentration treatment, and reconcentration may be carried out.

In the present invention, when acrylamide is prepared by bringing acrylonitrile into contact with water in the presence of a copper-based catalyst to hydrate acrylonitrile, a compound having an active methylene group and an acidic group in one molecule or a salt of the compound is allowed to be present in the synthetic reaction system. The active methylene group is a methylene group having the formula of X-CH$_2$-Y wherein each of X and Y is an electron attractive group such as NO$_2$, CN, COR, COAr, CONHR, CONHAr, CO$_2$R, CO$_2$H, SO$_2$, S, Ar and quaternary pyridinium, wherein R is an alkyl group and Ar is an aryl group, as described in Organic Reactions, John Wiley & Sons, Inc, Vol. 15, p. 222–223 (1967).

The compound which can be used in the present invention has the acidic group in addition to the above-mentioned active methylene group, and examples of the acidic group include a carboxylic group, a sulfonic group, a sulfinic group, a phosphonic group and a phosphinic group. Among these acidic groups, the carboxylic group and the sulfonic group which have the function as the acidic group also correspond to X and Y of the above-mentioned formula. Hence, the compound in which each of X and Y is the carboxylic group or the sulfonic group does not have to possess the acidic group. This kind of compound is preferable, because it conveniently has a simple structure and is easily available.

Furthermore, salts of these acidic groups, for example, sodium salts and the like can also be used. Examples of the compound in which X and Y each is also the acidic group include malonic acid, malonic monoester, malonic acid amide, cyanoacetic acid, cyanoacetic acid amide, acetoacetic acid, acetaldehydesulfonic acid, acetonesulfonic acid, sulfoacetic acid, sulfoacetic ester and sulfoacetic acid amide.

Among these compounds, α-substituted acetic acids in which the α position carbon of acetic acid is replaced with the above-mentioned functional group X or Y, i.e., malonic acid, malonic monoester, cyanoacetic, acid and the like are particularly preferable, because they are effective and easily available.

No particular restriction is put on the content of the compound, but in order to improve the sufficient water solubility and the molecular weight characteristics of the acrylamide polymer and in order to inhibit the excessive load of a purification step, the content of the compound is usually in a range of from 10 to 10,000 ppm, preferably 50 to 5,000 ppm based on the weight of a reaction solution.

As a technique of allowing the compound to be present in the reaction system, there are a way of dissolving the compound in material water or material acrylonitrile and then adding the dissolved compound, a way of dissolving the compound in a small amount of water, and a way of directly introducing the compound to the reactor or the reaction solution.

Furthermore, the compound having the active methylene group and the acidic group in one molecule or the salt of the compound can be added to a reaction solution obtained by the hydration reaction or a concentrated aqueous solution containing acrylamide in place of the reaction system, and this procedure is also a preferable embodiment.

In the present invention, the compound added to the synthetic-system can be removed by bringing the compound into contact with an anion exchange resin in the purification step. No particular restriction is put on the kind of anion exchange resin, but a weakly basic or a medially basic anion exchange resin can be preferably used. Examples of the anion exchange resin include microporous type weakly basic resins such as Lewatit MP62 (trade name, made by Bayer AG), Diaion WA20 (trade name, made by Mitsubish Chemical Industries, Ltd.) and Dowex 66 (trade name, made by Dow Chemical Co.), a gel type weakly basic resin such as Lewatit OC1059 (trade name, made by Bayer AG), gel type medially basic resins such as Lewatit MP64 (trade name, made by Bayer AG) and Amberlight IRA68 (trade name, Japan Organo Co., Ltd.), and a microporous type medially basic resin such as Dowex WRG2 (trade name, made by Dow Chemical Co.). These commercially available resins can be used after sufficiently washed with water, but it is preferable that they are subjected to a pretreatment with a dilute alkali, washed with water, and then used. With regard to a strongly basic anion exchange resin, its regeneration is difficult, and during the feed of the solution, acrylamide itself partially hydrolyzes to form acrylic acid, so that the exchange capacity of the resin noticeably deteriorates, and acrylamide is liable to polymerize between resin layers. Nevertheless, the strongly basic anion exchange resin is also usable.

The ion exchange resin can be used as a fixed layer such as a filling layer to continuously come in contact with an aqueous acrylamide solution and to purify the same, or the resin can be utilized in a batch system. However, the employment of the former is desirable, because of a good purification efficiency, an easy operation and the like. When the thus obtained acrylamide is homopolymerized or copolymerized with another comonomer, an acrylamide polymer having a remarkably improved water solubility and a sufficiently high molecular weight can be obtained.

Next, a high-molecular weight acrylamide polymer which can be used as a flocculant can be prepared as follows.

Acrylamide can be used singly or together with another vinyl polymerization type comonomer. Examples of the comonomer include acrylic acid, methacrylic acid and water-soluble salts thereof; alkylamino alkyl esters of acrylic acid and methacrylic acid and quaternary ammonium derivatives thereof; N-(dimethylaminopropyl)methacrylamide and quaternary ammonium derivatives thereof; vinyl acetate; and acrylonitrile. The mixing ratio of the comonomer to acrylamide is usually 100 mols or less, preferably 50 mols or less based on 100 mols of acrylamide.

The polymerization of acrylamide and the comonomer is carried out by a well-known manner such as aqueous solution polymerization or emulsion polymerization. Next, reference will be made to a typical procedure of the aqueous solution polymerization which has been used most extensively.

The total concentration of acrylamide and the comonomer is usually in a range of from 5 to 60% by weight. As a polymerization initiator, there can be used peroxides such as potassium persulfate, ammonium persulfate, hydrogen peroxide and benzoyl peroxide; azo-based free radical initiators such as azobisisobutyronitrile, 2,2'-azobis(4-amidinopropane) dihydrochloride and 4,4'-azobis(sodium 4-cyanovalerianate); and the so-called redox catalysts using the above-mentioned peroxides and reducing agents such as sodium bisulfite, triethanolamine and ammonium ferrous sulfate.

In the case that the total concentration of acrylamide and the comonomer is 15% by weight or more and the molecular weight of the obtained polymer is as high as 10,000,000 or more, a process involving heat insulating polymerization is usually employed, because it is difficult to control the temperature of the polymerization reaction by cooling or the like.

In this case, the temperature of the polymerization system rises by polymerization heat together with the progress of the polymerization. The preferable temperature at the start of the polymerization is often selected within a range of from −5° to 40° C., and the temperature at the end of the reaction reaches, for example, a high temperature of from 55° to 100° C.

In order to obtain a molecular weight of 10,000,000 or more, particularly a high-molecular weight of about 15,000,000, the total concentration of acrylamide and the comonomer, the kind and concentration of polymerization initiator to be used and the reaction temperature are contrived. Also in order to control the content of unreacted acrylamide to a trace amount of 0.2% by weight or less, a similar contrivance is made. In particular, many methods of using two or more kinds of polymerization initiators at different temperatures have been suggested and practiced.

The acrylamide polymer obtained by the above-mentioned polymerization reaction is a water-containing gel, i.e., a rubbery gel containing water substantially as it is which has been used to form an aqueous solution of acrylamide and the comonomer. In general, for the purpose of obtaining a dry powder product, a treatment such as the extraction of water, dehydration by heating and drying, or the crushing or grinding of the water-containing gel or the dry gel is carried out. Prior to this treatment or in the middle of the treatment, caustic soda may be kneaded with the water-containing gel, followed by heating, to convert part of amide groups into carboxyl groups, thereby chemically modifying the acrylamide polymer.

In accordance with the above-mentioned procedure, a acrylamide polymer having a high-molecular weight can be formed, the unreacted monomer can be decreased, and the polymer can be converted into the dry powder. In a certain case, however, as a result of the chemical modification, the sparingly water-soluble polymer is often formed and it tends to lose value as a commercial product such as a flocculant.

In order to solve this problem, a manner of adding an insolubilization inhibitor, a manner of using a specific polymerization initiator, or a manner of drying the water-containing gel under specific conditions is carried out before, while or after the polymerization reaction.

A process for preparing acrylamide according to the present invention summarily comprises the hydration reaction, the distillation operation, the various purification treatments and other additional steps as described above, and the obtained acrylamide can be fed to the manufacture of the above-mentioned high-molecular weight acrylamide polymer.

Next, the present invention will be described in more detail with reference to examples, but the scope of the present invention should not be limited to these examples.

EXAMPLE 1

Preparation of Acrylamide

Acrylonitrile was subjected to a hydration reaction in the presence of a copper-based catalyst by the following procedure to obtain acrylamide.
Catalyst for hydration reaction
A Raney copper alloy having a granular size of 80 mesh or less was developed with caustic soda, and then washed to prepare a Raney copper catalyst. During the preparation and in subsequent handling, the contact of the catalyst with a gas containing oxygen such as air was avoided.
Catalytic hydration reaction
400 g of the above-mentioned catalyst was placed in a SUS reactor having a volume of about 2 liters equipped with a stirrer and a catalyst separator therein, and acrylonitrile and water from which dissolved oxygen was beforehand removed by the use of a nitrogen gas were then fed at flow rates of 600 g/hr and 900 g/hr, respectively, and a reaction was carried out at 120° C. Afterward, malonic acid was added to the solution so that the concentration of malonic acid might be 150 ppm to the solution. The reaction solution was stirred together with a catalyst to become a suspension, and this suspension was then passed through the catalyst separator to take out the substantially catalyst-free solution from the reactor. This reaction was continued for 3 days.
Concentration
The obtained reaction solution was concentrated under reduced pressure by a batchwise, technique so that the total amount of unreacted acrylonitrile and a part of unreacted water were distilled off, thereby obtaining an aqueous acrylamide solution having a concentration of about 50% by weight. The thus obtained aqueous acrylamide solution contained copper.

Copper removal treatment

A glass column was filled with 150 ml of a strongly acidic cation exchange resin Lewatit SP112 (trade name, made by Bayer AG) which was made an H type by a pretreatment with dilute hydrochloric acid in accordance with a conventional procedure, and the aqueous acrylamide solution obtained by the above-mentioned concentration treatment was then passed through the glass column at 900 ml/hr. In the obtained solution, a copper content was 0.01 ppm or less, and a pH was in the range of 3.5 to 4.0.

Additive removal treatment

A glass column was filled with 150 ml of a weakly basic anion exchange resin Lewatit MP62 (trade name, made by Bayer AG) which was made an OH type by a pretreatment with dilute caustic soda in accordance with a conventional procedure, and the aqueous acrylamide solution obtained by the above-mentioned copper removal treatment was then passed through the glass column at 900 ml/hr. In the obtained solution, malonic acid was not detected, and a pH was in the range of about 6.5.

Preparation of acrylamide polymer:

The aqueous acrylamide solution obtained by the above-mentioned procedure was polymerized in the following procedure to obtain an acrylamide polymer.

Water was added to the aqueous acrylamide solution so that its concentration might be 20% by weight, and 500 g of the aqueous acrylamide solution was then placed in a 1 l polyethylene container. Afterward, nitrogen was blown into the solution to remove dissolved oxygen therefrom, while a solution temperature was maintained at 18° C., and the solution was then immediately poured into a foamed styrol heat insulating block.

Next, $200 \times 10^{-6}$ mpm (a molar ratio to acrylamide) of 4,4'-azobis(sodium 4-cyanovalerianate), $200 \times 10^{-6}$ mpm of dimethylaminopropionitrile and $80 \times 10^{-6}$ mpm of ammonium persulfate were each dissolved in a small amount of water, and they were then promptly poured into the above-mentioned solution in this order. To these reagents, a nitrogen gas was beforehand blown, and during, before and after the introduction of the these reagents, a small amount of the nitrogen gas was blown into the above-mentioned polyethylene container to prevent an oxygen gas from getting into the solution. After the introduction of the reagents and an induction period of several minutes, it was observed that the temperature in the polyethylene container rose, and so the feed of the nitrogen gas was stopped. When the temperature reached a peak of about 70° C. after about 100 minutes, the polyethylene container was taken out from the heat insulating block, immersed in water at 97° C. for 2 hours, and then immersed in cold water to cool it.

The thus obtained water-containing gel of an acrylamide polymer was divided into small masses, and they were then mashed by chopper, dried with hot air at 100° C. for 2 hours, and then ground by a high-speed rotary blade grinder to obtain an acrylamide polymer in the state of a dry powder. Furthermore, this polymer was put through a sieve to collect the polymer having a size of 32 to 42 mesh as polymer samples for a subsequent test. The water contents of the polymer samples were determined on the basis of a weight reduction by overnight drying with hot air at 125° C., and as a result, the water contents of these polymer samples were all about 10% by weight.

Tests of acrylamide polymer:

The water solubility and the standard viscosity of the polymer samples obtained by the above-mentioned procedure were measured as follows.

Water solubility

The water solubility was measured as follows. 600 ml of water was put into a 1 liter beaker, and 0.66 g (pure content=0.6 g) of the polymer sample was added, while water was stirred by a stirring blade having a certain shape. Next, stirring was carried out at 400 rpm for 2 hours, and the obtained solution was filtered through a wire gauze of 150 mesh. Thus, the water solubility was judged from the amount of insolubles and filtering characteristics. That is to say, evaluation was made as follows. ⊙ means the solution which could be completely dissolved; ○ means the solution which could be nearly completely dissolved; Δ means the solution in which the insolubles were present but they could be separated by filtration; and X means the solution in which the passage of a filtrate was slow and the filtration of the insolubles was practically impossible.

If having a molecular weight of about 15,000,000 or more and a solubility of ○ or higher, the acrylamide polymer has so high a quality as to be used as a flocculant. The acrylamide polymer having the solubility of Δ can be used as a paper agent, but it is not desirable as the flocculants. The acrylamide polymer having the solubility of X is not usable in most uses, and it has no commercial value.

Molecular weight

The molecular weight was determined as follows. Some aqueous acrylamide polymer solutions having different concentrations were prepared by the use of the filtrate obtained by the same procedure as described above, and 1 mol of sodium nitrate was added to each aqueous acrylamide polymer solution. Afterward, an intrinsic viscosity was measured by the use of a capillary viscometer, and the molecular weight was calculated as follows.

Intrinsic viscosity=$3.73 \times 10^{-4} \times$[weight average molecular weight]$^{0.66}$ The filtrate obtained in the above-mentioned solubility test was an aqueous polymer solution having a concentration of 0.1% by weight in the case that the water solubility was good. One mol of sodium chloride was added to this aqueous polymer solution, and a viscosity was measured at a rotor revolution of 60 rpm at 25° C. by the use of a BL viscometer and a BL adapter (standard viscosity). The standard viscosity obtained by such a procedure was used as a value concerned with the molecular weight, and so it was also used in this example.

Evaluation results of polymer

According to evaluation made in the above-mentioned manner, the water solubility of the obtained polymer was good and could be judged to be ⊙, and its standard viscosity was 6.0 cps (estimated molecular weight=17,200,000).

EXAMPLES 2 TO 10

The same procedure as in Example 1 was carried out except that in a catalytic hydration reaction of Example 1, the amount of malonic acid to be added to a material solution was changed and malonic acid was replaced with other additives as shown in Table 1, and that in an additive removal treatment, resins were changed as shown in Table 1. In acrylamides obtained in the respective examples, the additives were not detected. According to this evaluation, the finally obtained acrylamide polymers were excellent in water solubility and had sufficient molecular weights, as in Example 1.

COMPARATIVE EXAMPLES 1 TO 3

The same procedure as in Example 1 was carried out except that in a catalytic hydration reaction of Example 1, malonic acid to be added to a material solution was not added, and that other additives shown in Table 1 were used. In acrylamides obtained in the respective comparative examples, the additives were not detected, but the water solubility of any finally obtained acrylamide polymers was not satisfactory.

COMPARATIVE EXAMPLE 4

The same procedure as in Example 1 was carried out except that in place of malonic acid, m-cresol was added so that its concentration might be 100 ppm. In the obtained acrylamide, the additive was detected, and so any polymerization evaluation was not done.

COMPARATIVE EXAMPLE 5

The same procedure as in Example 1 was carried out except that in a catalytic hydration reaction of Example 1, as an additive, m-cresol was added so that its concentration might be 100 ppm to a material solution, and that in an additive removal treatment, a strongly basic anion exchange resin MP 500 was used. In obtained acrylamide, the additive was not detected. The water solubility of the finally obtained acrylamide polymer was not satisfactory.

COMPARATIVE EXAMPLE 6

The same procedure as in Example 1 was carried out except that in a catalytic hydration reaction of Example 1, as an additive, m-cresol was added so that its concentration might be 1,000 ppm to a material solution, and that in an additive removal treatment, a strongly basic anion exchange resin MP 500 was used. However, during the additive removal treatment, an aqueous acrylamide solution was inconveniently polymerized in a resin layer.

COMPARATIVE EXAMPLE 7

The same procedure as in Example 1 was carried out except that in a catalytic hydration reaction of Example 1, as an additive, urea was added so that its concentration might be 600 ppm to a material solution. In obtained acrylamide, the additive was not detected. The water solubility of the finally obtained acrylamide polymer was not satisfactory.

COMPARATIVE EXAMPLE 8

The same procedure as in Example 1 was carried out except that in a catalytic hydration reaction of Example 1, glycine was added so that its concentration might be 750 ppm to a material solution. However, the hydration reaction of acrylonitrile scarcely proceeded.

TABLE 1

| | Additive | Amount of Additive (ppm) | Conversion of Acrylonitrile (%) | Removal of Additive | | Evaluation of polymer | |
| --- | --- | --- | --- | --- | --- | --- | --- |
| | | | | Used Resin | Conc. of Additive (ppm) | Solubility | Standard viscosity (cps) |
| Example 1 | Malonic Acid | 150 | 60.0 | MP62 | N.D. (Note 1) | ⊙ | 6.0 (Note 2) |
| Example 2 | Malonic Acid | 1000 | 58.9 | MP62 | N.D. | ⊙ | 5.9 |
| Example 3 | Malonic Acid | 150 | 60.2 | OC1059 | N.D. | ⊙ | 6.0 |
| Example 4 | Sodium Malonate | 870 | 58.6 | MP62 | N.D. | ○ | 5.8 |
| Example 5 | Cyanoacetic Acid | 160 | 60.1 | MP62 | N.D. | ⊙ | 6.0 |
| Example 6 | Cyanoacetic Acid | 160 | 59.3 | OC1059 | N.D. | ○ | 6.1 |
| Example 7 | Cyanoacetic Acid | 160 | 61.1 | WA20 | N.D. | ○ | 6.0 |
| Example 8 | Acetoacetic Acid | 200 | 59.9 | MP62 | N.D. | ○ | 5.9 |
| Example 9 | Acetosulfunic Acid | 200 | 56.4 | MP62 | N.D. | ○ | 5.8 |
| Example 10 | Sulfoacetic Acid Amide | 200 | 57.1 | MP62 | N.D. | ○ | 5.8 |
| Comp. Ex. 1 | None | 0 | 49.8 | MP62 | N.D. | X | Measurement was impossible |
| Comp. Ex. 2 | Acrylic Acid | 140 | 60.1 | MP62 | N.D. | Δ | 5.8 |
| Comp. Ex. 3 | Acetic Acid | 120 | 52.2 | MP62 | N.D. | X | Measurement was impossible |
| Comp. Ex. 4 | m-cresol | 100 | 56.4 | MP62 | 80 | | |
| Comp. Ex. 5 | m-cresol | 100 | 57.2 | MP500 | N.D. | Δ | 6.0 |
| Comp. Ex. 6 | m-cresol | 1000 | 60.0 | MP500 | Polymerized while fed | | |
| Comp. Ex. 7 | Urea | 600 | 44.4 | MP62 | N.D. | X | Measurement was impossible |
| Comp. Ex. 8 | Glycine | 750 | Reaction did not occur | | | | |

(Note 1):
N.D. means that the additive was not detected.
(Note 2):
The acrylamide polymer of Example 1 estimates as a molecular weight of about 17,200,000.

What is claimed is:

1. A process for preparing acrylamide by subjecting acrylonitrile to a hydration reaction in a reaction system including the presence of copper based catalyst wherein the improvement comprises allowing a compound having an active methylene group and an acidic group in one molecule or a salt of the compound to be present in the reaction system wherein the active methylene group is defined by the formula $X$-$CH_2$-$Y$ wherein each of X and Y is selected from the group consisting of $NO_2$, CN, COR, COAr, CONHR, CONHAr, $CO_2R$, $CO_2H$, $SO_2$, S, Ar and quaternary pyridinium wherein R is an alkyl group and Ar is an aryl group.

2. The process for preparing acrylamide according to claim 1, wherein the amount of the compound having the active methylene group and the acidic group in one molecule or the salt of the compound is in a range of 10 to 10,000 ppm based on the weight of a reaction solution.

3. The process for preparing acrylamide according to claim 1, wherein the acidic group is a carboxylic group or a sulfonic group.

4. The process for preparing acrylamide according to claim 1, wherein the compound having the active methylene group and the acidic group in one molecule or the salt of the compound is an s-substituted acetic acid or its salt.

5. The process for preparing acrylamide according to claim 4, wherein the s-substituted acetic acid or its salt is malonic acid, cyanoacetic acid, or its salt.

6. A process for preparing acrylamide which comprises the steps of subjecting acrylonitrile to a hydration reaction in the presence of a copper-based catalyst wherein the improvement comprises conducting the reaction in the presence of a compound having an active methylene group and an acidic group in one molecule or a salt of the compound, and then bringing a solution containing acrylamide into contact with a weakly basic or a medially basic anion exchange resin wherein the active methylene group is defined by the formula $X$-$CH_2$-$Y$ wherein each of X and Y is selected from the group consisting of $NO_2$, CN, COR, COAr, CONHR, CONHAr, $CO_2R$, $CO_2R$, $CO_2H$, $SO_2$, S, Ar and quaternary pyridinium wherein R is an alkyl group and Ar is an aryl group.

7. A process for preparing acrylamide which comprises the steps of subjecting acrylonitrile to a hydration reaction in the presence of a copper-based catalyst wherein the improvement comprises allowing a compound having an active methylene group and an acidic group in one molecule or a salt of the compound to be present in a solution containing obtained acrylamide, and then bringing the solution containing acrylamide into contact with a weakly basic or a medically basic anion exchange resin wherein the active methylene group is defined by the formula $X$-$CH_2$-$Y$ wherein each of X and Y is selected from the group consisting of $NO_2$, CN, COR, COAr, CONHR, CONHAr, $CO_2R$, $CO_2H$, $SO_2$, S, Ar and quaternary pyridinium wherein R is an alkyl group and Ar is an aryl group.

8. The process of claim 1 wherein said compound is selected from the group consisting of malonic acid, malonic monoester, malonic acid amide, cyanoacetic acid, cyanoacetic acid amide, acetoacetic acid, acetaldehydesulfonic acid, acetonesulfonic acid, sulfoacetic acid, sulfoacetic ester and sulfoacetic acid amide.

9. The process of claim 1 wherein said compound is selected from the group consisting of malonic acid, sodium malonate, cyanoacetic acid, acetoacetic acid, acetosulfinic acid and sulfoacetic acid amide.

10. The process of claim 6 wherein said compound is selected from the group consisting of malonic acid, malonic monoester, malonic acid amide, cyanoacetic acid, cyanoacetic acid amide, acetoacetic acid, acetaldehydesulfonic acid, acetonesulfonic acid, sulfoacetic acid, sulfoacetic ester and sulfoacetic acid amide.

11. The process of claim 6 wherein said compound is selected from the group consisting of malonic acid, sodium malonate, cyanoacetic acid, acetoacetic acid, acctosulfinic acid and sulfoacetic acid amide.

12. The process of claim 7 wherein said compound is selected from the group consisting of malonic acid, malonic monoester, malonic acid amide, cyanoacetic acid, cyanoacetic acid amide, acetoacetic acid, acetaldehydesulfonic acid, acetonesulfonic acid, sulfoacetic acid, sulfoacctic ester and sulfoacetic acid amide.

13. The process of claim 7 wherein said compound is selected from the group consisting of malonic acid, sodium malonate, cyanoacetic acid, acetoacetic acid, acetosulfinic acid and sulfoacetic acid amide.

* * * * *

UNITED STATES PATENT AND TRADEMARK OFFICE
CERTIFICATE OF CORRECTION

PATENT NO. : 5,534,655
DATED : July 9, 1996
INVENTOR(S) : Yoshihiko Kambara, et al It is certified that error appears in the above-identified patent and that said Letters Patent is hereby corrected as shown below:

On the title page, item [30] Foreign Application Priority Data, shouls read

March 2, 1994 [JP] Japan .............. 6-032094

Under Other Documents, please insert the following information as filed in the Information Disclosure Statement of February 23, 1995:

Khim, Tekhonol, 1983 (3), pp.23-24 (ABSTRACT)

IN THE CLAIMS

Col., 13, in claim 1, line 4, delete "copper based" and insert --copper-based--.

in claim 4, line 24, delete "s-substituted" and insert --$\sigma$-substituted--.

in claim 5, line 26, delete "s-substituted" and insert --$\sigma$-substituted--.

Col., 14, in claim 12, line 37, delete "sulfoacctic" and insert --sulfoacetic--.

Signed and Sealed this

Ninth Day of December, 1997

*Attest:*

BRUCE LEHMAN

*Attesting Officer*  Commissioner of Patents and Trademarks